(12) United States Patent
Bohsung et al.

(10) Patent No.: US 9,750,956 B2
(45) Date of Patent: Sep. 5, 2017

(54) DETERMINING AN IRRADIATION PLAN FOR A PARTICLE IRRADIATION UNIT

(71) Applicant: SIEMENS AKTIENGESELLSCHAFT, München (DE)

(72) Inventors: Jörg Bohsung, Heidelberg (DE); Thilo Elsässer, Buckenhof (DE); Sven Oliver Grözinger, Hausen (DE); Iwan Kawrakow, Ljulin (BG); Johann Kim, Erlangen (DE); Robert Neuhauser, Neufahrn (DE); Eike Rietzel, Weiterstadt (DE); Oliver Thilmann, Augsburg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 166 days.

(21) Appl. No.: 14/414,345

(22) PCT Filed: Jun. 7, 2013

(86) PCT No.: PCT/EP2013/061834
§ 371 (c)(1),
(2) Date: Jan. 12, 2015

(87) PCT Pub. No.: WO2014/009073
PCT Pub. Date: Jan. 16, 2014

(65) Prior Publication Data
US 2015/0196781 A1 Jul. 16, 2015

(30) Foreign Application Priority Data
Jul. 13, 2012 (DE) .................. 10 2012 212 341

(51) Int. Cl.
*A61N 5/00* (2006.01)
*A61N 5/10* (2006.01)

(52) U.S. Cl.
CPC ......... *A61N 5/1067* (2013.01); *A61N 5/1031* (2013.01); *A61N 2005/1087* (2013.01)

(58) Field of Classification Search
CPC ................ A61N 5/1067; A61N 5/1031; A61N 2005/1087
(Continued)

(56) References Cited

U.S. PATENT DOCUMENTS 8,598,546 B2 * 12/2013 Bert .................... A61N 5/10
250/492.1
2010/0213394 A1 * 8/2010 Fieres .................. A61N 5/1031
250/492.3
(Continued)

FOREIGN PATENT DOCUMENTS

DE 102008009765 9/2009
DE 102009010284 9/2010
(Continued)

OTHER PUBLICATIONS

German Office Action cited in DE102012212341.5, mailed Apr. 6, 2013.
(Continued)

*Primary Examiner* — Michael Maskell
(74) *Attorney, Agent, or Firm* — Lempia Summerfield Katz LLC

(57) ABSTRACT

A target volume within a test object is irradiated according to an irradiation plan with a particle beam using a particle irradiation unit. The irradiation plan is determined in order to apply the energy of the particle beam in the target volume according to a predetermined dose distribution. In addition, a boundary condition is specified for at least one of the isoenergy layers and the irradiation plan is additionally specified such that the boundary condition is met for the at least one isoenergy layer. The boundary condition includes one or more of a minimum boundary energy, a maximum boundary energy, a minimum grid point number, a minimum total particle number, a minimum total dose, a minimum dose contribution to a total dose to be administered, a minimum contribution to a target function which is calcu-
(Continued)

lated for determining the irradiation plan, and a minimum dose compensation error.

18 Claims, 3 Drawing Sheets

(58) Field of Classification Search
USPC .......................................... 250/492.1–492.3
See application file for complete search history.

(56) References Cited

U.S. PATENT DOCUMENTS

| | | | |
|---|---|---|---|
| 2010/0327188 A1* | 12/2010 | Bert | ......................... A61N 5/10 250/492.3 |
| 2012/0187314 A1 | 7/2012 | Bert et al. | |
| 2015/0217135 A1* | 8/2015 | Bohsung | .............. A61N 5/1031 250/492.3 |

FOREIGN PATENT DOCUMENTS

| | | |
|---|---|---|
| DE | 102009033297 | 1/2011 |
| DE | 102009043548 | 3/2011 |
| EP | 2392383 | 12/2011 |
| WO | WO2011039022 | 4/2011 |

OTHER PUBLICATIONS

Kanematsu et al., Treatment Planning for the Layer-Stacking Irradiation System for Three-Dimensional Conformal Heavy-Ion Radiotherapy, 2002, pp. 2823-2829, vol. 12, No. 12, Med. Phys.
Search Report and Written Opinion cited in PCT/EP2013/061834, mailed Sep. 26, 2013.

* cited by examiner

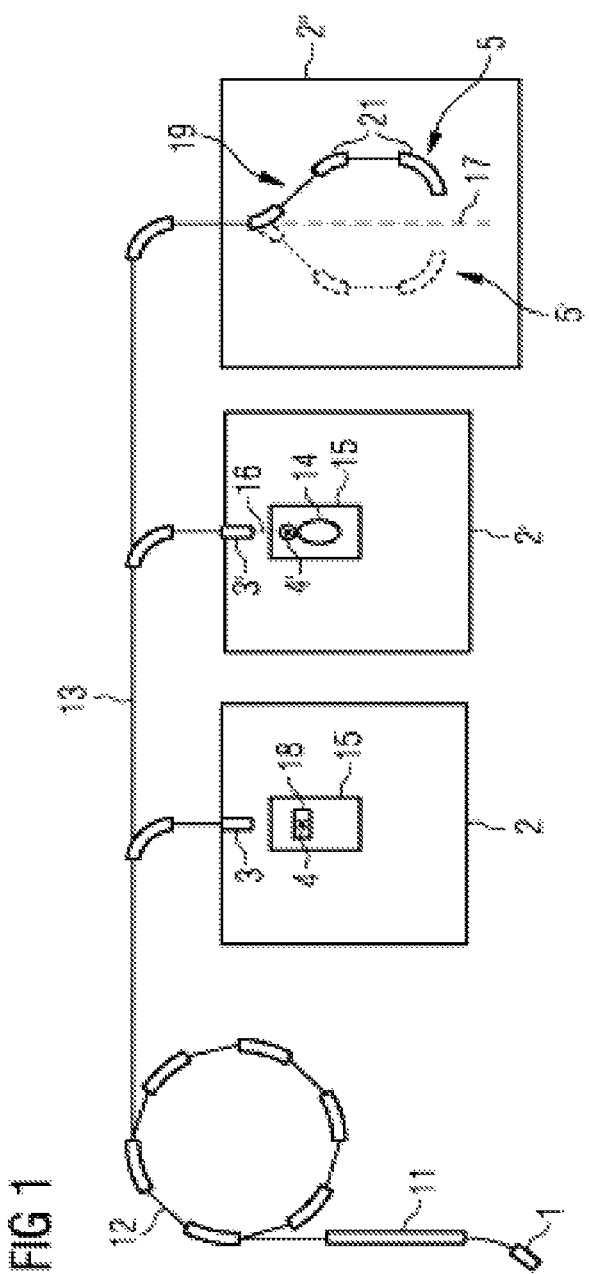

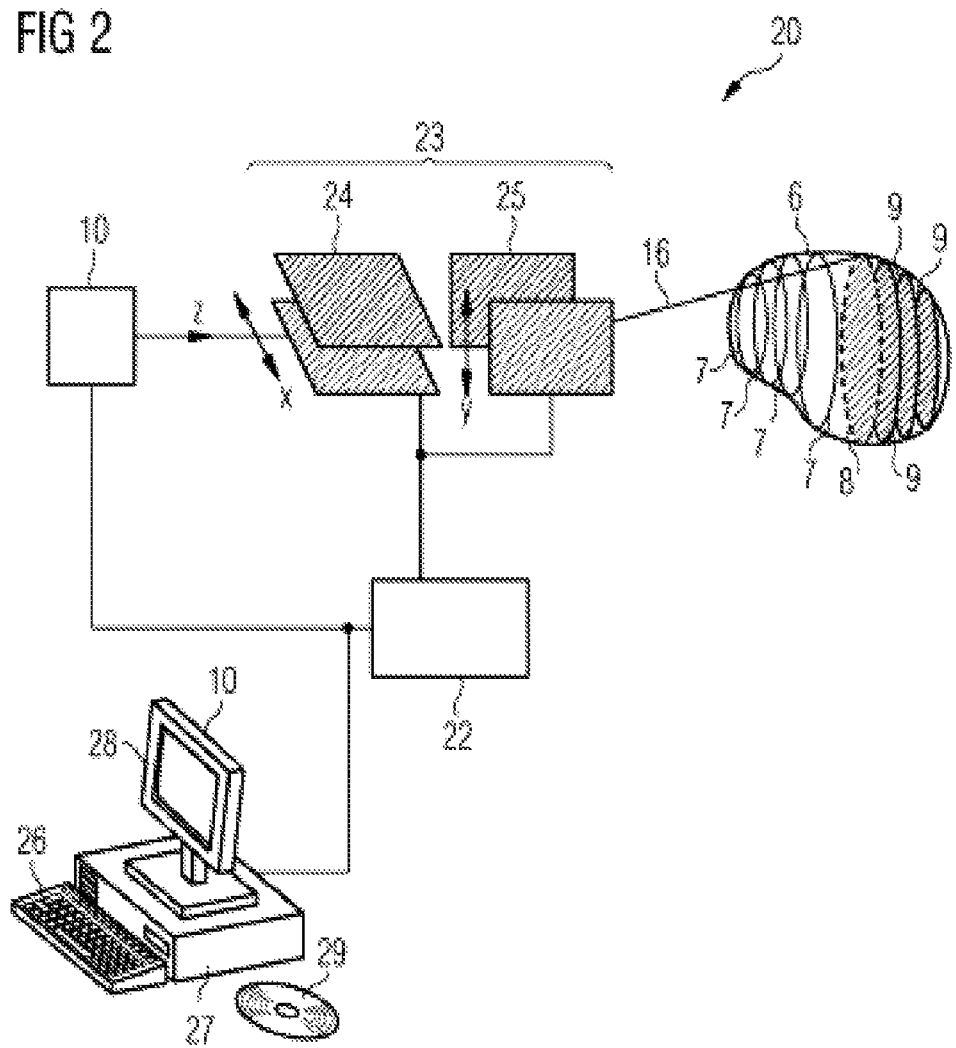

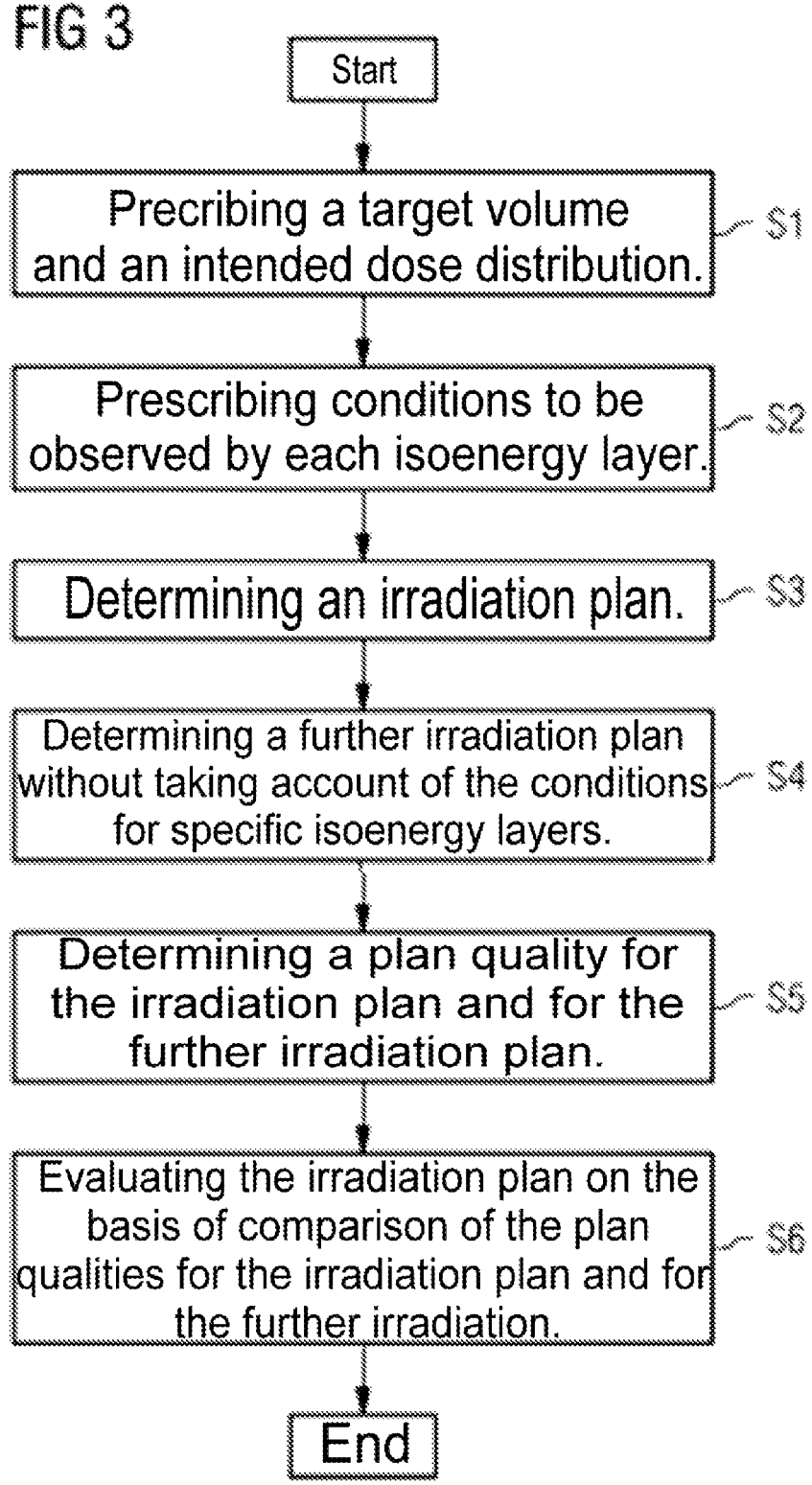

DETERMINING AN IRRADIATION PLAN FOR A PARTICLE IRRADIATION UNIT

CROSS-REFERENCE TO RELATED APPLICATIONS

The present patent document is a §371 nationalization of PCT Application Serial Number PCT/EP2013/061834, filed Jun. 7, 2013, designating the United States, which is hereby incorporated by reference, and this patent document also claims the benefit of DE 10 2012 212 341.5, filed on Jul. 13, 2012, which is also hereby incorporated by reference.

TECHNICAL FIELD

The present embodiments relate to a method and a device for determining an irradiation plan for a particle irradiation unit and an accordingly embodied particle irradiation unit.

BACKGROUND

By way of example, within the scope of therapy planning in particle radiotherapy, an irradiation plan that defines control parameters for irradiating an examination object is created in advance. The irradiation plan is used to plan the irradiation of an object in accordance with specific prescriptions (e.g., target volume or dose distribution).

Particle radiotherapy is a well-established method by which, in particular, tissue afflicted by tumor diseases is irradiated. In the case of particle radiotherapy, charged particles, such as, e.g., electrons, protons, or carbon ions or other ions, or else photons or neutrons, are accelerated to high energies, shaped to make a particle beam and conveyed via a high-energy transportation system to one (or more) irradiation rooms. The target volume of the treatment object is irradiated by the particle beam in an irradiation room, wherein tissue outside of the target volume is necessarily also irradiated.

If accelerators with an active energy variation are used in particle radiotherapy, particle beams with different energies are used for irradiating the target volume. This leads to the formation of so-called isoenergy layers that may lie within, and outside of, the target volume. In an isoenergy layer, the particle beam applies particles with the same energy such that the particles of the particle beam to be positioned on the respective isoenergy layer respectively have an energy that differs from the energy of the particles for other isoenergy layers. Here, where possible, all particles for an isoenergy layer are applied with the aid of one spill (e.g., by a single accelerator fill) since loading or generating a new spill takes a number of seconds. In total, the interruption time for generating a new spill takes up a significant portion of the overall irradiation duration, depending on the number of particles to be applied. In order to provide a patient-friendly irradiation that is as short as possible, an accurate application of the dose in the target volume and the most economical operation of the particle irradiation unit are possible, it is necessary to keep the direct irradiation time (e.g., the time during which the patient is in fact exposed to the particle beam) and the overall irradiation duration (e.g., the time that the patient spends in the irradiation room) as short as possible. However, in so doing, it is necessary to consider the quality of the irradiation plan, which is ultimately to be assessed by the treating medical practitioner.

SUMMARY AND DESCRIPTION

The scope of the present invention is defined solely by the appended claims and is not affected to any degree by the statements within this summary. The present embodiments may obviate one or more of the drawbacks or limitations in the related art.

The present embodiments are posed with the problem of keeping the overall irradiation duration as short as possible, while maintaining an acceptable plan quality when determining an irradiation plan for a particle irradiation unit.

Within the scope of the present embodiments, a method for (in particular automatically) determining an irradiation plan for a particle irradiation unit is provided. Here, with the aid of the particle irradiation unit, a target volume within an examination object is irradiated by a particle beam in accordance with the irradiation plan. Here, proceeding from a prescribed target volume and a predetermined dose distribution (e.g., intended dose distribution) within this target volume, the irradiation plan is determined in order to deposit, or to apply, the dose of the particle beam into, or to, the target volume, which includes a plurality of isoenergy layers, with a high quality (e.g., as exactly as possible in accordance with the intended dose distribution) on the basis of the irradiation plan. Here, a boundary condition to be observed by the irradiation plan is specified for one or more isoenergy layers. Here, this boundary condition includes one or more of the conditions listed below.

1. Minimum Peak Energy

An isoenergy layer to be irradiated has at least a minimum peak energy. Expressed differently, those isoenergy layers for which the particle beam for the irradiation thereof would have an energy lying below the minimum peak energy are not irradiated (not taken into account by the irradiation plan).

Here, the condition in respect of the minimum peak energy may be defined in absolute (e.g., without taking into account the respective energies of the isoenergy layers) or relative (e.g., taking into account the respective energies of the isoenergy layers) terms. By way of example, if the 3 (n) isoenergy layers with the lowest energies are not intended to be taken into account or irradiated, the minimum peak energy is defined relative to the energy of the isoenergy layer with the third lowest (n lowest) energy and, for example, lies slightly above the energy (of the particles) of the isoenergy layer with the third lowest (n lowest) energy. By contrast, an absolute definition of the minimum peak energy does not consider the respective energies of the isoenergy layers, and so, for example, all isoenergy layers below a predetermined energy (e.g., 150 MeV) are not irradiated, with this criterion being independent of how many, or which percentage, of the isoenergy layers are not irradiated in that case.

2. Maximum Peak Energy

Energy lying above the maximum peak energy is not required for irradiating an isoenergy layer. Expressed differently, those isoenergy layers for which the particle beam for the irradiation thereof would have an energy lying above the maximum peak energy are not irradiated (not taken into account by the irradiation plan).

Here, the maximum peak energy may be defined in absolute (e.g., without taking into account the respective energies of the isoenergy layers) or relative (e.g., taking into account the respective energies of the isoenergy layers) terms. By way of example, if the 3 (n) isoenergy layers with the highest energies are not intended to be taken into account or irradiated, the maximum peak energy is defined relative to the energy of the isoenergy layer with the third highest (n highest) energy and lies slightly below the energy (e.g., of the particles) of the isoenergy layer with the third highest (n highest) energy. By contrast, an absolute definition of the maximum peak energy does not consider the respective energies of the isoenergy layers.

3. Maximum Number of Raster Points

In accordance with this condition, only isoenergy layers whose number of raster points does not lie below the minimum number of raster points are irradiated.

Here, a raster point is understood to refer to a point in a plane through the isocenter that is orthogonal to the particle beam. The particle beam is in each case directed to a raster point, which therefore determines the direction of the particle beam.

If the number of raster points for an isoenergy layer is very small, the plan quality of the irradiation plan is not significantly improved by irradiating this isoenergy layer. As a result of this condition, the irradiation of such an isoenergy layer is avoided, as a result of which the irradiation time of a patient may advantageously be reduced.

4. Minimum Overall Number of Particles

In accordance with this condition, only isoenergy layers whose overall number of particles does not lie below the minimum overall number of particles are irradiated.

5. Minimum Overall Dose

In accordance with this condition, only isoenergy layers for which the overall dose applied in the respective isoenergy layer is at least not smaller than the minimum overall dose are irradiated.

6. Minimum Dose Contribution to an Overall Dose to be Applied

In accordance with this condition, only isoenergy layers are irradiated for which the dose applied in the respective isoenergy layer has at least the minimum dose contribution to the overall dose to be applied overall (e.g., for all isoenergy layers) in the target volume. Here, this minimum dose contribution may be a specific percentage of the overall dose to be applied in the target volume. Then, only those isoenergy layers are irradiated in which the ratio of the dose applied in the respective isoenergy layer to the overall dose to be applied in the target volume corresponds to at least this percentage.

What may happen during the optimization on the basis of plan quality criteria in an irradiation plan according to the prior art is that the optimized overall number of particles for an isoenergy layer is so low that the overall dose applied in the isoenergy layer is negligible compared to the overall dose for the complete irradiation plan or at least contributes a value that is negligibly small in respect of the plan quality. What this condition avoids is that such an isoenergy layer is irradiated, as a result of which the overall irradiation time may be reduced by 3 to 5 s (a time for irradiating an isoenergy layer).

7. Minimum Contribution to a Target Function that is Calculated for Determining the Irradiation Plan The contribution to the target function may be determined for each isoenergy layer. In accordance with this condition, only isoenergy layers for which the contribution to the target function corresponds to at least the minimum contribution are irradiated.

8. Minimum Dose Compensation Error

The dose compensation error specifies the extent of an error that occurs as a result of the non-irradiation of a specific isoenergy layer despite corresponding compensation by the irradiated isoenergy layers. In accordance with this condition, only isoenergy layers for which the dose compensation error is not smaller than the minimum dose compensation error are irradiated.

So that the irradiation plan determined observes the boundary condition or one or more of the aforementioned conditions, the corresponding conditions are, in particular, already taken into account when producing the irradiation plan. That is to say, care is already taken during the production of the irradiation plan that no isoenergy layer breaks the boundary condition or one or more of the conditions.

It is also possible to create the irradiation plan without considering the boundary condition in a first act and then to remove all isoenergy layers that do not meet the prescribed boundary condition from irradiation in a second act. Subsequently, it is optionally possible for the irradiation plan to be re-optimized after the removed isoenergy layers have been excluded.

The target function is optimized for determining the irradiation plan, wherein each (irradiated) isoenergy layer supplies a specific contribution to this target function. The contribution of the respective isoenergy layer may in this case be composed of a sum of contributions benefiting the target function (e.g., dose contribution for the overall dose) and contributions deteriorating the target function (e.g., time duration of the irradiation, irradiation of healthy tissue). Therefore, when checking whether an isoenergy layer contributes at least the minimum contribution to the target function, only a benefiting contribution of the respective isoenergy layer is taken into account. That is to say, an isoenergy layer that (overall) only supplies a contribution deteriorating the target function has not met the condition.

Here, it is possible for an individual boundary condition to be prescribed for each isoenergy layer such that each isoenergy layer observes one or more conditions that are individually tailored to the respective isoenergy layer.

However, it is also possible for one or more of the conditions listed above to apply for each isoenergy layer such that, in this case, virtually the same condition(s) applies/apply for all isoenergy layers.

The evaluation of the irradiation plan produced may be undertaken by one of the following procedures.

In accordance with a first embodiment for evaluating the irradiation plan, a further irradiation plan may be determined, wherein, for determining this further irradiation plan, the boundary condition is lifted for one isoenergy layer or for a plurality of those isoenergy layers, in which no irradiation takes place in accordance with the irradiation plan to be evaluated since the boundary condition is broken. As a result, the further irradiation plan is determined without a restriction by the boundary condition for the one or more isoenergy layers being taken into account. In other words, the one or more isoenergy layers, which are not irradiated in accordance with the irradiation plan to be evaluated, may be provided for irradiation in the further irradiation plan, without the boundary condition being considered in the process. In order to evaluate the irradiation plan, a plan quality of the irradiation plan is firstly produced, which is substantially dependent on the obtained dose distribution. This plan quality is compared to a further plan quality that is produced for the further irradiation plan, wherein this further plan quality also substantially depends on the dose distribution obtained by the further irradiation plan. In the normal case, the evaluation of the irradiation plan may be considered to improve as the difference between the plan quality and the further plan quality decreases.

In an extreme case, the further irradiation plan in this first embodiment may be produced without taking account of any boundary condition in respect of any isoenergy layer.

Expressed differently, a check as to how strongly the plan quality of the irradiation plan deteriorates as a result of the boundary condition being observed is carried out in accordance with the first embodiment for the purposes of evaluating the irradiation plan produced.

In accordance with a second embodiment for evaluating the irradiation plan produced, it is possible to determine a dose distribution that is applied in accordance with the irradiation plan to be evaluated. This dose distribution is now compared to the predetermined dose distribution, wherein the result of this comparison corresponds to the evaluation of the irradiation plan.

The more the dose distribution determined for the irradiation plan produced corresponds to the predetermined dose distribution, the better the evaluation of the irradiation plan produced may be.

In accordance with a third embodiment for evaluating the irradiation plan produced, one or more planning results that are produced for the irradiation plan are used. Here, the planning result or the planning results is/are selected from the following group of planning results. (1) A dose/volume histogram is produced for the irradiation plan to be evaluated. (2) A specification of how much of the dose is applied in the target volume according to the irradiation plan. Here, the dose applied in the target volume according to the irradiation plan may correspond to the best possible extent to the prescribed dose distribution or intended dose distribution. This planning result also contains a specification about tolerance limits in respect of the dose distribution within the target volume being observed (e.g., "dose constraints of planning target volume"). (3) A specification of how much of the dose is applied in at least one organ at risk of the examination object according to the irradiation plan to be evaluated. By way of example, the information as to whether specific tolerance limits are observed in respect of the organs at risk may be derived from this specification.

This evaluation on the basis of one or more of the planning results listed above may also be used for determining the plan quality of the further irradiation plan.

The target function that is calculated for determining the irradiation plan may include a penalty term, wherein this penalty term reduces the quality of the target function further as a distance in accordance with the irradiation plan to the respective condition decreases.

These circumstances are intended to be explained again in more detail below.

In order to determine the irradiation plan, an optimization algorithm is used to determine an ideal function value of the target function in accordance with an embodiment. Here, the target function considers firstly the contributions or the terms benefiting the ideal function value that, e.g., assume an optimum when the dose applied in accordance with the irradiation plan corresponds to the intended dose. By taking into account the penalty term, the function value of the target function, and hence the evaluation of the irradiation plan to be produced, worsens the closer the irradiation plan gets to a limit or threshold defined by the condition to be observed with respect to one or more isoenergy layers. Accordingly, the penalty term forms a counterbalance for producing the irradiation plan in such a way that the predetermined conditions are observed. In other words, the predefined boundary condition is already, in the form of the penalty term, taken into account in the optimization algorithm, by which the target function is optimized.

In order to predetermine the boundary condition for the one or more isoenergy layers, the following procedure may be followed:

A preliminary irradiation plan is determined in order to apply the particle beam in accordance with the intended dose distribution in the target volume on the basis of this irradiation plan. Here, this preliminary irradiation plan is produced, in particular, without taking into account the boundary condition. The boundary condition to be observed when producing the actual irradiation plan is produced proceeding from the preliminary irradiation plan.

By virtue of the preliminary irradiation plan being produced for producing the boundary condition, the boundary condition (e.g., the minimum number of raster points, the minimum overall number of particles, the minimum overall dose, the minimum contribution to the target function, the minimum dose compensation error) may be determined in such a way that, e.g., a predetermined number (e.g., 10%) of the isoenergy layers that, according to the preliminary irradiation plan are to be irradiated, break the boundary condition or one of the conditions.

Within the scope of the present embodiments, provision is also made for a device for determining an irradiation plan for a particle irradiation unit. Here, depending on the determined irradiation plan, the particle irradiation unit irradiates a target volume within an examination object with a particle beam. The device includes an input, a computer, and an output. The target volume, a predetermined dose distribution (intended dose distribution) and a boundary condition for one or more of the isoenergy layers are prescribed for the device by the input. The computer determines the irradiation plan in such a way that the particles of the particle beam are delivered to the target volume that includes a plurality of isoenergy layers, in accordance with the predetermined dose distribution. The irradiation plan is output by the output. The computer of the device determines the irradiation plan additionally in such a way that the boundary condition is observed for the one isoenergy layer or for the plurality of isoenergy layers. Here, the boundary condition includes at least one of the conditions that were listed above in respect of the method.

The advantages of the device substantially correspond to the advantages of the method, which are explained in detail above, and so a repetition is refrained from here.

Moreover, the present embodiments provide a particle irradiation unit with a device.

Moreover, the present embodiments describe a computer program product, in particular software, which may be loaded into a memory of a programmable control apparatus or computer of a particle irradiation unit. By this computer program product, it is possible to execute all or various above-described embodiments of the method when the computer program product runs in the control apparatus. Here, the computer program product may require a program, e.g., libraries and auxiliary functions, for realizing the corresponding embodiments of the method. In other words, the claim directed to the computer program product may, in particular, protect software by which one of the above-described embodiments of the method may be executed, or which executes this embodiment. Here, the software may be a source code (e.g., C++), which still needs to be compiled and linked or only interpreted, or executable software code that, for execution purposes, still needs to be loaded into the corresponding computer or the control apparatus.

Finally, the present embodiments disclose an electronically readable data medium, (e.g., a DVD, magnetic tape, or USB stick), on which electronically readable control information, in particular software (cf. above), is stored. If this control information (e.g., software) is read from the data medium and stored in the control device or a computing unit of a particle irradiation unit, all embodiments of the method described above may be performed.

The selection of the conditions to be observed or the precise determination or definition of the individual condition may be prescribed here by a user, either interactively or by a configuration setting.

As a result of prescribing and observing the boundary condition, the number of isoenergy layers to be irradiated may be reduced compared to the prior art. As a result, the overall irradiation duration may be significantly shortened, which leads to greater comfort for the patient and to an increase in the effectiveness of the particle irradiation unit. The introduction advantageously requires no intervention in the beam application or in the accelerator itself, since this relates to a programming embodiment. As a result of a selectability of the conditions and a display of the effects on the quality of the irradiation plan, it is moreover advantageously possible to find an ideal compromise on a case-by-case basis between a reduced overall irradiation duration and the quality of the irradiation plan.

In particular, the present embodiments are suitable for increasing the patient throughput in particle radiotherapy. Naturally, the present embodiments are not restricted to this field of application and, in principle, may be used wherever energy or a dose is applied in a target volume by particles.

BRIEF DESCRIPTION OF THE DRAWINGS

FIG. 1 schematically depicts an embodiment of an overview of the design of a particle irradiation unit.

FIG. 2 schematically depicts an embodiment of how a target volume is irradiated by a particle irradiation unit.

FIG. 3 depicts a flowchart of an embodiment of a method.

DETAILED DESCRIPTION

The particle irradiation unit 20 depicted schematically in FIG. 1 irradiates a patient 14 (see irradiation room 2') lying on a positioning device 15 (e.g., a table) with a beam including particles 16, which is referred to as a particle beam 16 below. By way of example, such a particle beam 16 may be used to irradiate a tumor in the patient 14 using high-energy particles. However, it is also possible to use the particle irradiation unit 20 to irradiate an inanimate object 18, as is depicted in irradiation room 2 using the example of a water phantom 18.

By way of example, protons, pions, helium ions, carbon ions, but also ions from other elements are used as particles. To this end, the corresponding particles are generated in a particle source or ion source 1 and accelerated to a first energy level in a pre-accelerator 11 (e.g., a linear accelerator). The particles are subsequently accelerated to an energy required for the irradiation in a ring accelerator 12 (e.g., a synchrotron or cyclotron). The particle beam emerging from the ring accelerator 12 is transported by a high-energy beam transportation system 13 to one or more irradiation rooms 2, 2', 2", and used therein for irradiating a target volume in a patient 14. The irradiation is effected from a fixed direction, and so the body 14, 18 to be irradiated is arranged in advance in a spatially fixed manner by the positioning device 15 in the irradiation room 2, 2'. The irradiation rooms 2, 2' are therefore also referred to as so-called "fixed beam" rooms. By contrast, there is a gantry 19 in irradiation room 2", which gantry is arranged in a manner movable about an axis 17, in particular in a rotatable manner, wherein the body to be irradiated may be irradiated from different directions (e.g., with different fields) by the gantry. To this end, the particle beam 16 is accordingly directed to the body to be irradiated with the aid of a beam guide 21 in the gantry 19. FIG. 1 depicts two positions 5, 5', although a plurality of positions are possible.

In the irradiation rooms 2, 2', the particle beam 16 emerges from a beam outlet 3, 3' and impacts on the body 14 and 18, respectively, in which the target volume to be irradiated is situated. Here, the target volume normally lies in the isocenter 4, 4' of the respective irradiation room 2, 2'.

FIG. 2 schematically depicts a target volume 6, which is irradiated by a particle beam 16 generated by a particle irradiation unit 20. In addition to an irradiation planning device 10, the particle irradiation unit 20 includes a beam generation device 30, a raster scan apparatus 23 and a controller 22 for the raster scan apparatus 23. The raster scan apparatus 23 in turn includes a first particle deflection 24 and a second particle deflection 25, which in each case include magnets in particular. With the aid of the two particle deflections 24, 25, the particle beam 16 may be deflected both horizontally and vertically, which is depicted by the mutually perpendicular arrows x, y. Therefore, the raster scan apparatus 23 is able to direct the particle beam 16 to any point $(x_i, y_i)$ on a surface within the x,y-plane. Each of these points is, together with the respectively inserted particle energy, referred to as scan spot, raster point, or scan point. Accordingly, a raster point is determined, firstly, by the alignment of the particle beam 16 (x- or y-direction) and, secondly, by the particle energy thereof. In other words, there are a plurality of raster points with different particle energies for specific x- and y-coordinates. Here, as it were, the particle energy determines (taking into account the irradiated body that, e.g., is established by a CT recording) the coordinate in the z-direction (perpendicular to the x- and y-axes), wherein, for example, what applies is that the z-position of the Bragg peak lies ever further in the direction of the particle beam 16 within the target volume 6 as the particle energy increases. However, since the penetration depth is dependent on the tissue or material through which the particle beam 16 passes, the above relationship only applies exactly to the same x- and y-positions.

Here, the Bragg peak is understood to provide the point or region at which the particle beam applies the greatest portion of its dose along the trajectory thereof.

The target volume 6 to be irradiated by the particle beam 16 is in this case irradiated in the form of isoenergy layers 7-9. In this case, particles with the same energy are respectively applied in the raster points of the same isoenergy layer 7-9. Under the assumption that the particle beam 16 passes through a homogeneous volume on its path to the corresponding isoenergy layer 7-9, the isoenergy layers 7-9 lie perpendicular to the z-axis, as depicted in a simplified manner in FIG. 2.

In order to set the particle beam 16 to a corresponding isoenergy layer 7-9 (e.g., in order to position the Bragg peak on an isoenergy layer 7-9), the particles of the particle beam 16 are in each case assigned an appropriate initial energy by virtue of the particles being accelerated to a velocity corresponding to this initial energy. Here, the initial energy describes the energy of a particle that the particle has prior to impact on the object 14 or 18. In order to irradiate the isoenergy layer 7 lying closest to the beam outlet 3, 3' (e.g., lying furthest to the left in FIG. 2), use is made of the particles with the lowest energy, whereas, in order to irradiate the isoenergy layer 9 that is arranged furthest from the beam outlet 3, 3' (e.g., furthest to the right in FIG. 2), use is made of the particles with the highest energy.

In order to irradiate the whole target volume 6, the isoenergy layers 7-9 are irradiated in succession, wherein, for example, a start is made at the isoenergy layer 9 situated furthest from the beam outlet 3, 3' and the process is then continued with the respectively adjacent isoenergy layer. In order to irradiate specific raster points within the same isoenergy layer 7-9 with different amounts of energy, the period of time during which the respective raster point is irradiated by the particle beam 16 is, in particular, varied. As the duration of irradiation by the particle beam 16 for the corresponding raster point increases, more energy (e.g., a higher dose) is deposited in the corresponding raster point.

In the target volume 6 depicted in FIG. 2, the isoenergy layer 8 is currently irradiated by the particle beam 16, while the three isoenergy layers 9 have already been irradiated and the four isoenergy layers 7 lying further to the left (in FIG. 2) are still waiting to be irradiated.

Before the target volume 6 is irradiated, an irradiation plan, by which the scanning of the target volume 6 by the particle beam 16 is effected, is generated. Here, the irradiation plan in particular determines the control parameters for controlling the particle irradiation unit 20. Here, the irradiation plan is generated with the aid of an irradiation planning device 10 (e.g., a PC).

In order to perform the actual irradiation, the irradiation plan is forwarded from the irradiation planning device 10 to the beam generation device 30 and to the controller 22 of the raster scan apparatus 23. In FIG. 2, the irradiation planning device 10 is depicted virtually as a component of the particle irradiation unit 20. Naturally, it is just as easily possible that the irradiation plan generated by the irradiation planning device 10 is loaded onto a data medium 29, by which the irradiation plan is then loaded into the particle irradiation unit 20. In this case, the irradiation planning device 10 and the particle irradiation unit 20 need not be linked by a communication-technical device. Moreover, a certain amount of time, (e.g., a number of days), may lie between generating the irradiation plan and performing the irradiation on the basis of the irradiation plan.

In order to generate the irradiation plan, the irradiation planning device 10 requires the location and dimensions of the target volume 6 to be irradiated (e.g., of a tumor to be irradiated). Moreover, the nature of the tissue through which the particle beam 16 passes on the way to the target volume 6 is required when irradiating a patient 14. By way of example, this information may be established by a computed tomography or magnetic resonance imaging scanner and then transmitted to the irradiation planning device 10 by appropriate an input 26. Proceeding from this information and a predetermined dose distribution (e.g., intended dose distribution), the irradiation planning device 10 determines the irradiation plan with the aid of the computer 27 thereof. In particular, the irradiation plan in this case specifies how many particles with a specific energy are to be applied at a raster point.

A patient needs to be fixed during the irradiation in order to preclude, to the greatest possible extent, a movement of the target volume 6. For this reason, the irradiation duration may be kept as short as possible. Moreover, a short irradiation duration advantageously enables a higher patient throughput. On the other hand, the dose distribution in accordance with the irradiation plan may correspond to the intended dose distribution to the best possible extent. By virtue of the number of irradiated isoenergy layers being smaller than in the prior art as only isoenergy layers that observe the boundary condition are irradiated, an irradiation plan has a shorter overall irradiation duration.

In FIG. 3, a flowchart is depicted.

In act 51, the target volume and the intended dose distribution are prescribed, while the conditions to be observed by each isoenergy layer (e.g., minimum number of raster points, minimum overall number of particles, minimum overall dose) are prescribed in act S2. Proceeding from these prescriptions, an irradiation plan is determined in act S3.

In order to evaluate this irradiation plan determined in act S3, a further irradiation plan is produced in act S4. When producing this further irradiation plan, these conditions are suspended for specific ones of those isoenergy layers that are not irradiated according to the irradiation plan determined in act S3 as they do not meet the prescribed conditions. In other words, the prescribed conditions in respect of the specific isoenergy layers are not checked when producing the further irradiation plan, and so the further irradiation plan is produced with a greater degree of freedom.

Subsequently, a plan quality is respectively determined in act S5 for both the irradiation plan and the further irradiation plan, which plan quality, in particular, makes a statement regarding how far the dose distribution planned by the respective irradiation plan corresponds to the intended dose distribution. The irradiation plan is evaluated in act S6 on the basis of a comparison between the plan quality of the irradiation plan and the plan quality of the further irradiation plan.

As a result of this comparison of the plan qualities, it is possible, for example, to examine the change in the three-dimensional dose distribution if, in accordance with the irradiation plan, specific ones (or all) of the isoenergy layers marked for removal are interactively rejoined, for example by a user interface, by virtue of the observance of the conditions for these isoenergy layers being suspended. In order to simplify the decision regarding which isoenergy layers are to be rejoined, it is possible to display the time that is saved when the respective isoenergy layer is not irradiated. The comparison of the plan qualities of the irradiation plan and of the further irradiation plan may hereby be supported by displaying specific planning results (e.g., dose/volume histograms) in order to provide the user with a further decision aid.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining an irradiation plan for a particle irradiation unit, wherein the particle irradiation unit is used to irradiate a target volume within an examination object with a particle beam depending on the irradiation plan, the method comprising:

prescribing the target volume and a predetermined dose distribution; and determining the irradiation plan in order to apply the particle beam in accordance with the predetermined dose distribution in the target volume, the target volume comprising a plurality of isoenergy layers, wherein a boundary condition is prescribed for at least one of the isoenergy layers, wherein the irradiation plan is determined such that the boundary condition for the at least one isoenergy layer is observed, wherein the boundary condition comprises at least one of the following conditions:
a minimum peak energy,
a maximum peak energy,
a minimum number of raster points,
a minimum overall number of particles,
a minimum overall dose,
a minimum dose contribution to an overall dose to be applied,
a minimum contribution to a target function calculated for determining the irradiation plan, and
a minimum dose compensation error, wherein the dose compensation error specifies an error that occurs as a result of the non-irradiation of the respective isoenergy layer despite corresponding compensation by the irradiated isoenergy layers, and wherein at least one individual boundary condition is prescribed for each isoenergy layer of the plurality of isoenergy layers.

2. The method as claimed in claim 1, wherein a same condition is prescribed for each isoenergy layer in respect of at least one of the conditions.

3. The method as claimed in claim 1, further comprising:
determining a further irradiation plan,
wherein, for the determining of the further irradiation plan, the boundary condition is lifted for at least one specific one of the isoenergy layers, in which no particles are applied in accordance with the irradiation plan since the boundary condition is broken, such that the further irradiation plan is determined without there being a restriction by the boundary condition in respect of the at least one specific isoenergy layer, and
wherein a plan quality of the irradiation plan depending on the dose distribution is compared to a further plan quality of the further irradiation plan depending on the dose distribution for evaluating the irradiation plan.

4. The method as claimed in claim 1, wherein a dose distribution is determined,
wherein the dose distribution is applied in accordance with the irradiation plan, and
wherein the dose distribution is compared to the predetermined dose distribution for evaluating the irradiation plan.

5. The method as claimed in claim 4, wherein at least one planning result of a group of planning results for the irradiation plan and for a further irradiation plan is determined for evaluating the irradiation plan, and
wherein the group of planning results comprises:
a dose/volume histogram,
a specification of how much of the dose is applied in the target volume according to the irradiation plan, and
a specification of how much of the dose is applied in at least one organ at risk of the examination object according to the irradiation plan.

6. The method as claimed in claim 1, wherein the target function, which is calculated for determining the irradiation plan, comprises a penalty term, and
wherein the penalty term reduces a quality of a function value to be optimized of the target function further as a distance in accordance with the irradiation plan to the respective condition decreases.

7. The method as claimed in claim 1, wherein a preliminary irradiation plan is determined in order to apply the particle beam in the target volume in accordance with the predetermined dose distribution, and
wherein the boundary condition is prescribed depending on the preliminary irradiation plan.

8. A device for determining an irradiation plan for a particle irradiation unit, wherein the particle irradiation unit is used to irradiate a target volume within an examination object with a particle beam depending on the irradiation plan, the device comprising:
an input;
a computer; and
an output, wherein the target volume and a predetermined dose distribution are prescribable for the device by the input,
wherein the computer is configured to determine the irradiation plan in order to apply the particle beam in the target volume comprising a plurality of isoenergy layers, in accordance with the predetermined dose distribution,
wherein the output is configured to output the irradiation plan,
wherein a boundary condition for at least one of the isoenergy layers is prescribable for the device by the input, where the computer is configured to additionally determine the irradiation plan such that the boundary condition for the at least one isoenergy layer is observed,
wherein the boundary condition comprises at least one of the following conditions:
a minimum peak energy,
a maximum peak energy,
a minimum number of raster points,
a minimum overall number of particles,
a minimum overall dose,
a minimum dose contribution to an overall dose to be applied,
a minimum contribution to a target function calculated for determining the irradiation plan, and
a minimum dose compensation error, wherein the dose compensation error specifies an error that occurs as a result of the non-irradiation of the respective isoenergy layer despite corresponding compensation by the irradiated isoenergy layers, and wherein at least one individual boundary condition is prescribed for each isoenergy layer of the plurality of isoenergy layers.

9. A computer program product comprising a non-transitory computer-readable storage medium that stores instructions executable by a control apparatus of a particle irradiation unit, the instructions comprising:
prescribing a target volume and a predetermined dose distribution; and
determining an irradiation plan in order to apply a particle beam in accordance with the predetermined dose distribution in the target volume, the target volume comprising a plurality of isoenergy layers,
wherein a boundary condition is prescribed for at least one of the isoenergy layers, wherein the irradiation plan is determined such that the boundary condition for the at least one isoenergy layer is observed, wherein the boundary condition comprises at least one of the following conditions:
- a minimum peak energy,
- a maximum peak energy,
- a minimum number of raster points,
- a minimum overall number of particles,
- a minimum overall dose,
- a minimum dose contribution to an overall dose to be applied,
- a minimum contribution to a target function calculated for determining the irradiation plan, and
- a minimum dose compensation error, wherein the dose compensation error specifies an error that occurs as a result of the non-irradiation of the respective isoenergy layer despite corresponding compensation by the irradiated isoenergy layers, and wherein at least one individual boundary condition is prescribed for each isoenergy layer of the plurality of isoenergy layers.

10. An electronically readable data medium with electronically readable control information stored thereon which is configured in such a way that, when the data medium is used in a control apparatus of a particle irradiation unit, the data medium is configured to at least perform:
prescribe a target volume and a predetermined dose distribution; and
determine an irradiation plan in order to apply a particle beam in accordance with the predetermined dose distribution in the target volume, the target volume comprising a plurality of isoenergy layers,
wherein a boundary condition is prescribed for at least one of the isoenergy layers,
wherein the irradiation plan is determined such that the boundary condition for the at least one isoenergy layer is observed,
wherein the boundary condition comprises at least one of the following conditions:
- a minimum peak energy,
- a maximum peak energy,
- a minimum number of raster points,
- a minimum overall number of particles,
- a minimum overall dose,
- a minimum dose contribution to an overall dose to be applied,
- a minimum contribution to a target function calculated for determining the irradiation plan, and
- a minimum dose compensation error, wherein the dose compensation error specifies an error that occurs as a result of the non-irradiation of the respective isoenergy layer despite corresponding compensation by the irradiated isoenergy layers, and wherein at least one individual boundary condition is prescribed for each isoenergy layer of the plurality of isoenergy layers.

11. The method as claimed in claim 3, wherein an individual boundary condition is prescribed for each isoenergy layer.

12. The method as claimed in claim 3, wherein a same condition is prescribed for each isoenergy layer in respect of at least one of the conditions.

13. The method as claimed in claim 3, wherein at least one planning result of a group of planning results for the irradiation plan and for the further irradiation plan is determined for evaluating the irradiation plan,
wherein the group of planning results comprises:
a dose/volume histogram,
a specification of how much of the dose is applied in the target volume according to the irradiation plan, and
a specification of how much of the dose is applied in at least one organ at risk of the examination object according to the irradiation plan.

14. The method as claimed in claim 13, wherein the target function, which is calculated for determining the irradiation plan, comprises a penalty term, and
wherein the penalty term reduces a quality of a function value to be optimized of the target function further as a distance in accordance with the irradiation plan to the respective condition decreases.

15. The method as claimed in claim 13, wherein a preliminary irradiation plan is determined in order to apply the particle beam in the target volume in accordance with the predetermined dose distribution, and
wherein the boundary condition is prescribed depending on the preliminary irradiation plan.

16. The method as claimed in claim 3, wherein the target function, which is calculated for determining the irradiation plan, comprises a penalty term, and
wherein the penalty term reduces a quality of a function value to be optimized of the target function further as a distance in accordance with the irradiation plan to the respective condition decreases.

17. The method as claimed in claim 3, wherein a preliminary irradiation plan is determined in order to apply the particle beam in the target volume in accordance with the predetermined dose distribution, and
wherein the boundary condition is prescribed depending on the preliminary irradiation plan.

18. A method for determining an irradiation plan for a particle irradiation unit, wherein the particle irradiation unit is used to irradiate a target volume within an examination object with a particle beam depending on the irradiation plan, the method comprising:
prescribing the target volume and a predetermined dose distribution;
determining the irradiation plan in order to apply the particle beam in accordance with the predetermined dose distribution in the target volume, the target volume comprising a plurality of isoenergy layers, wherein a boundary condition is prescribed for at least one isoenergy layer of the plurality of isoenergy layers; and
determining a further irradiation plan, wherein, for the determining of the further irradiation plan, the boundary condition is lifted for at least one specific one isoenergy layer of the plurality of isoenergy layers, in which no particles are applied in accordance with the irradiation plan since the boundary condition is broken, such that the further irradiation plan is determined without there being a restriction by the boundary condition with respect to the at least one specific isoenergy layer, and wherein a plan quality of the irradiation plan depending on the dose distribution is compared to a further plan quality of the further irradiation plan depending on the dose distribution for evaluating the irradiation plan,
wherein the irradiation plan is determined such that the boundary condition for the at least one isoenergy layer is observed, and
wherein the boundary condition comprises at least one of the following conditions:

a minimum peak energy,
a maximum peak energy,
a minimum number of raster points,
a minimum overall number of particles,
a minimum overall dose,
a minimum dose contribution to an overall dose to be applied,
a minimum contribution to a target function calculated for determining the irradiation plan, and
a minimum dose compensation error, wherein the dose compensation error specifies an error that occurs as a result of the non-irradiation of the respective isoenergy layer despite corresponding compensation by the irradiated isoenergy layers.

* * * * *